United States Patent [19]

Masreliez

[11] Patent Number: 5,043,560
[45] Date of Patent: Aug. 27, 1991

[54] TEMPERATURE CONTROL OF A HEATED PROBE

[76] Inventor: C. Johan Masreliez, 3301 181st Pl. NE., Redmond, Wash. 98052

[21] Appl. No.: 415,171

[22] Filed: Sep. 29, 1989

[51] Int. Cl.[5] .............................................. H05B 1/02
[52] U.S. Cl. ..................................... 219/497; 219/492; 219/501; 219/505; 323/235; 374/179
[58] Field of Search ............... 219/494, 492, 497, 499, 219/501, 505, 507, 509; 323/235, 236, 319

[56] References Cited

U.S. PATENT DOCUMENTS

| | | | |
|---|---|---|---|
| 3,002,077 | 9/1961 | Caliri | 219/26 |
| 3,698,394 | 10/1972 | Piper et al. | 128/303.1 |
| 3,789,190 | 1/1974 | Orosy et al. | 219/497 |
| 3,886,944 | 6/1975 | Jamshidi | 128/303.1 |
| 3,889,680 | 6/1975 | Armao | 128/303.1 |
| 4,074,719 | 2/1978 | Semm | 219/506 |
| 4,189,331 | 2/1980 | Roy | 148/6.31 |
| 4,392,827 | 7/1983 | Martin | 433/32 |
| 4,527,560 | 7/1985 | Masreliez | 219/233 |
| 4,546,239 | 10/1985 | Sugimori | 219/497 |
| 4,590,363 | 5/1986 | Bernard | 219/497 |
| 4,591,699 | 5/1986 | Sato | 219/497 |
| 4,628,169 | 12/1986 | Ch'ing-Lung | 219/68 |
| 4,636,619 | 1/1987 | Sugimori | 219/497 |
| 4,636,620 | 1/1987 | Wright et al. | 219/497 |
| 4,695,709 | 9/1987 | Sachs et al. | 219/505 |
| 4,745,263 | 5/1988 | Brooks | 219/497 |

*Primary Examiner*—Mark H. Paschall
*Attorney, Agent, or Firm*—Seed and Berry

[57] ABSTRACT

A method and apparatus for precisely controlling the temperature of a heated tip are disclosed. The temperature of a thermocouple within the tip is sensed at a selected rate. The sensed temperature is compared with a preselected temperature set by a user. The power provided to heat the tip is varied to cause the tip to achieve the selected temperature. If an AC power source is used, the temperature sensed at each zero crossing of the power source and the amount of power provided within that cycle is based on the temperaature of the tip sensed within the same cycle. The duration of time that heat is applied to the probe within the cycle is varied to achieve the desired temperature. If a DC power source is used, the temperature of the tip is sensed at selected intervals. The sensed temperature controls the amount of power provided to heat the tip. The exact temperature of the tip is thus advantageously controlled to provide the desired heating.

20 Claims, 8 Drawing Sheets 5,043,560

TEMPERATURE CONTROL OF A HEATED PROBE

TECHNICAL FIELD

This invention relates to controlling the temperature of a miniature heated probe and, more particularly, to a circuit and method for sensing the temperature at the tip of the probe and controlling the power to the probe to maintain a selected temperature.

BACKGROUND OF THE INVENTION

Accurate temperature control of a small, heated probe is required in many different environments. For example, in the surface mount technology of electronic chips, there is a need to solder very tiny leads onto boards without damaging the components or the narrow leads of the printed circuit board. The temperature of the soldering tip must be above a selected temperature but must not exceed a certain temperature range for a period of time. In dentistry, narrow, heated probes are used in root canal therapy when filling the root system with heat-softened gutta percha (natural rubber) or other substances. Heated tips are often used to cauterize blood vessels to prevent bleeding. The tips are frequently very small and require precise temperature control at the point of application.

Current technology suffers from significant constraints making it very difficult to develop a suitable miniature, heated probe that is temperature-controlled.

A heated medical or dental probe of this type is shown and described in U.S. Pat. No. 4,527,560 to the same inventor of the present application and is incorporated herein by reference.

Traditionally, a soldering iron includes a relatively large thermostatically controlled tip made from a material of good heat conductivity, usually copper. This tip acts as a heat reservoir from which the heat is conducted to a narrow soldering point. However, if this point becomes too narrow, it is mechanically weak and in addition tends to be easily destroyed by oxidation. At the same time, the amount of heat which can be conducted to the tip decreases the narrower the tip becomes. For these and other reasons, accurate measurement of the temperature of the tip and maintaining the temperature within a precise range is not possible with current technology.

U.S. Pat. No. 4,074,719, in columns 5 and 6 and FIG. 3, describes a device for causing blood coagulation. A thermocouple within the heating probe provides a voltage for determining the temperature. The probe of the prior art does not include a switch to switch the probe between the power supply and the thermocouple voltage sensor.

SUMMARY OF THE INVENTION

It is therefore an object of this invention to provide a circuit for accurately maintaining the temperature of a heated microprobe within a selected range.

It is another object of this invention to provide a method for controlling the power applied to a heated probe to achieve a selected temperature.

These and other objects of the invention, as will be apparent herein, are accomplished by construction of a tip having a conductive inner core member of a first material and a resistive heating member of a second material. The core member and the resistive heating member are connected to each other at the distal end of the tip. A thermocouple is formed in the tip by the junction of the core member and the heating member. The voltage generated at the thermocouple junction is indicative of the temperature at the distal end of the tip.

A sensing circuit is selectively coupled to the thermocouple formed between the inner core and the member for sensing the temperature of the tip based on the thermocouple voltage potential. An alternating current power source is selectively coupled to the core member for heating the tip by current passing through the resistive outer core layer. A switching circuit selectively couples the tip to either the power source for heating of the tip or to the sensing circuit for sensing the temperature of the tip.

The switching circuit couples the tip to the sensing circuit at each zero crossing of the alternating current power supply and disconnects the tip from the heating power source. The tip remains coupled to the sensing circuit for a selected time. The time period within each half-cycle when the probe is disconnected from the power supply is based on the difference in temperature between the tip and the preselected temperature set by the user. As the tip heats up, approaching the temperature selected by the user, the time period after the zero crossing until the tip is connected to the power supply becomes longer, gradually slowing down the heating of the tip until the selected temperature is reached.

Because the probe temperature is controlled by the percentage of power provided in each half cycle of the AC power supply, the temperature is accurately controlled. A further advantage is that the temperature quickly and smoothly reaches the operating temperature and is held at the proper temperature without excessive excursions from the selected temperature. Because the duty cycle is gradually varied as the tip temperature approaches the selected temperature and based on variations from the selected temperature, overheating by overshooting is selectively couples the tip to either the power source or avoided and excessive cooling is also avoided. In one embodiment, a DC power source heats the tip. A switch the temperature sensing and control circuit.

DETAILED DESCRIPTION OF THE INVENTION

Figure 1:
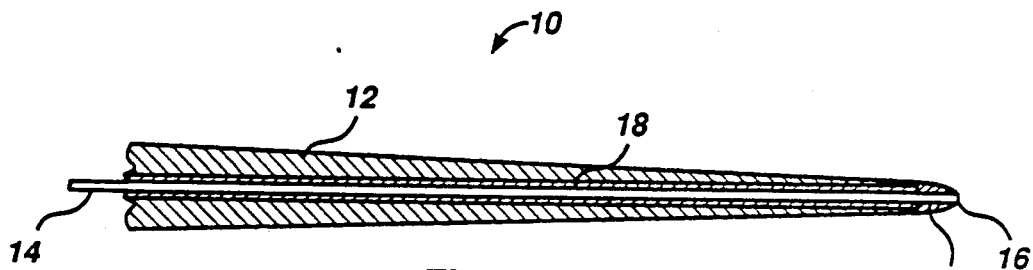
FIG. 1 is a typical longitudinal cross-sectional view of a tip of a probe for use with this invention.

As shown in FIG. 1, a tip 10 includes an inner core member 14 and resistive outer layer 12. The inner core member 14 is made of a first material, such as nickel-coated copper, and the resistive outer layer 12 of a second material, such as stainless steel, though other materials may be used for either member, if desired. The inner core member 14 and resistive outer layer 12 contact each other at a distal end 16 of the tip 10. An insulating layer 18 surrounds the core member 14 as it extends to the tip to electrically isolate the core member 14 from the resistive outer layer 12 except at the distal end of the tip. A thermocouple junction 22 is formed at the contact between the inner core member 14 and the resistive outer layer 12.

Figure 2:
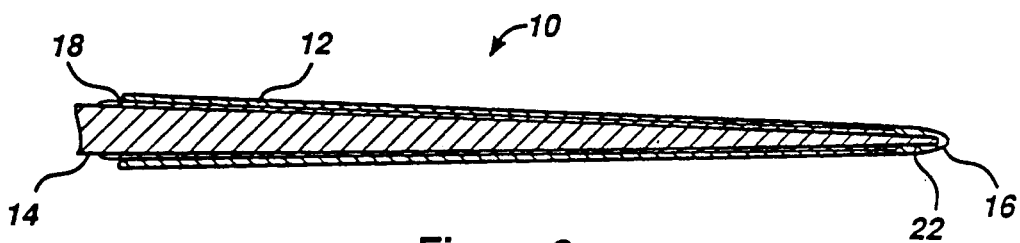
FIG. 2 is a longitudinal cross-sectional view of an alternative tip of a probe for use with this invention.

FIG. 2 is an alternative embodiment of a tip 10 operating on the same general principles as the tip 10 of FIG. 1. The tip 10 includes an inner conductive member 14, and a resistive outer layer 12, but differs from the tip of FIG. 1 because the core member 14 has a variable diameter and narrows towards the tip. An insulating member 18 extends between the inner member 14 and outer layer 12 except at a distal end 16. A thermocouple junction 22 is formed between the inner core member 14 and the resistive outer layer 12 of the tip 10.

The temperature of the tip 10 is measured by sensing the thermoelectric voltage potential between the conductive inner core member 14 and the resistive outer layer 12 within the distal end 16 of the tip itself at junction 22. For an inner core 14 of copper and an outer material 12 of stainless steel, the voltage is approximately 1.5 microvolts per degree Fahrenheit. As the temperature of the junction 22 varies, the thermoelectric voltage generated at this junction 22 will also vary, according to the well-known operating principles of thermocouples.

Figure 3:
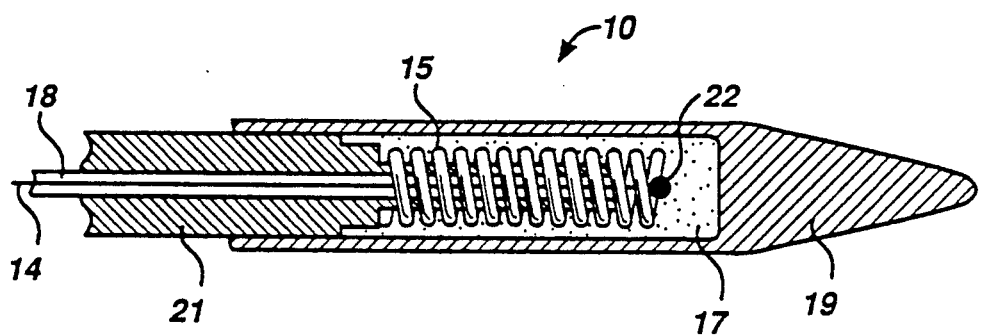
FIG. 3 is a longitudinal cross-sectional view of an alternative tip of a probe for use with this invention.

FIG. 3 illustrates an alternative embodiment of a heating tip 10. The heating tip 10 includes a power wire 14 coupled to a heating coil 15. A thermoconductor junction 22 is formed between the power wire 14 and the heating coil 17, the two wires being of a different material. The temperature of the thermoconductor junction 22 corresponds to the temperature of the heated member 19. The heating coil 15 is surrounded by electrically insulating ceramic filling material 17. The heating coil 15 is coupled to a grounding member 21. The grounding member 21 has a large cross-sectional area for the current and does not heat up significantly. The heating coil 15 and grounding member 21 may be of the same material if desired so that a thermocouple junction is not formed between them. A heated member 19 surrounds the ceramic material 17. No electrical current passes through the actual heating member which contacts the surface to be melted. The heating member 19 is electrically coupled to the outer grounding member 21 to provide grounding. In an alternative embodiment, the heated member 19 is thermally and electrically insulated from the conductive grounding member 21.

The heating coil 15 heats up when an electric current is passed therethrough, heating up the surrounding ceramic material 17 and the heated member 19. The heating coil 17 may be stainless steel, a nickel alloy or any other suitable material which achieves a high temperature when electric current is passed therethrough.

Figure 4:
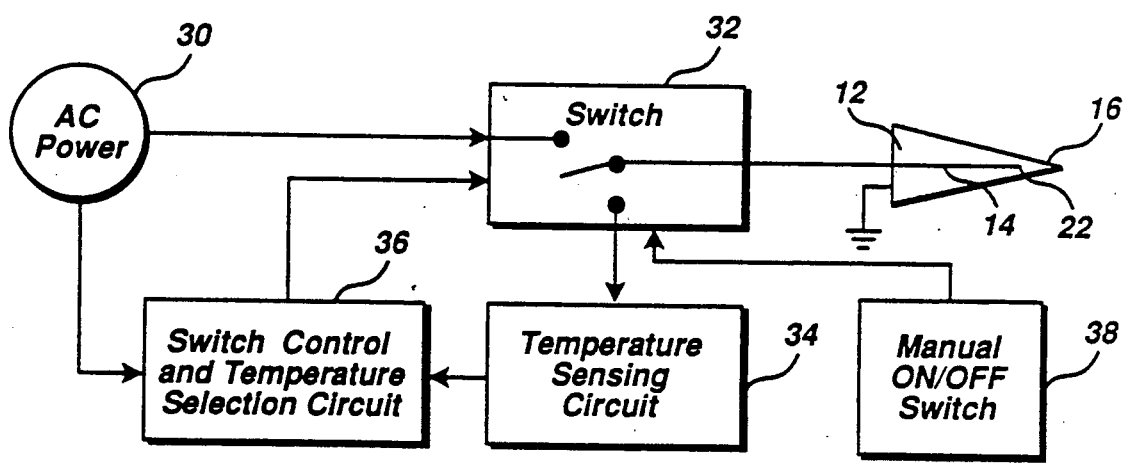
FIG. 4 is a block diagram of a circuit for accurately controlling the tip temperature according to the invention.

As shown in FIG. 4, switch 32 selectively couples the tip 10 to either the AC power supply 30 or to the temperature-sensing circuit 34. When the AC power supply 30 is coupled to the tip 10, the tip is heated. When the temperature-sensing circuit 34 is coupled to the tip 10, the voltage potential at junction 22 is sensed to determine the temperature of the tip. Because the voltage generated at the thermocouple junction 22 is small compared to the heating voltage passing through thermocoupled junction 22 when heating the tip, the thermocouple voltage is preferably measured when the heating current is not passing through the tip. When the probe tip 10 is coupled to the AC power supply 30, the switch 32 automatically disconnects the temperature-sensing circuit 34 from the tip 10. Similarly, when the switch 32 couples the tip 10 to the temperature-sensing circuit 34, the AC power supply 30 is disconnected from the tip 10.

Switch control and temperature selection circuit 36 controls the position of the switch 32 based on the temperature of the tip. The temperature-sensing circuit 34 senses the temperature of the tip 10 at thermocouple junction 22 during that portion of the cycle when the AC power supply 30 is not coupled to the tip 10. The manual on/off switch 38 permits a user to activate the heating of the tip 10 under control of circuits 34 and 36 or disable the switch 32 into the off position prevent it from heating.

The tip 10 is heated under control of the circuits of FIG. 4 as follows. A user activates the heating of tip 10 by placing the manual switch 38 into the on position. The user has previously set a temperature to which the tip 10 is heated. The switch 32 couples the tip 10 to the AC power supply 30 for a significant portion of each cycle heating the tip 10. The switch control circuit 36 disconnects the tip 10 from the power source 30 and couples it to the temperature sensing circuit 34 at least once each cycle. The time duration that the tip 10 is coupled to the power supply 30 within a cycle is based on the tip temperature to the preselected temperature set by the user. When the tip temperature is low, power is applied to tip 10 for the majority of a cycle. When the tip 10 is hotter, approaching the selected temperature, the switch control circuit 36 changes the position of switch 32 sooner in the cycle to provide less power to the tip 10. When the tip 10 reaches the selected temperature, the switch control circuit 36 couples the probe 10 to the AC power supply 30 only for a sufficient part of each cycle to maintain the temperature at the selected value. When the user has completed the task, manual on/off switch 38 permits a user to manually disconnect the tip from the AC power supply 30 to prevent heating. The manual on/off switch 38 may be a foot peddle 106, touch sensitive switch 114 in the handle (described later herein with respect to FIG. 5c), or other switch available in the art. The temperature sensed at the beginning of the cycle is input to the switch control circuit 36 for controlling the amount of power provided to the probe 10 within that same cycle. Rapid and accurate temperature control of the tip 10 is therefore provided.

Figure 5A:
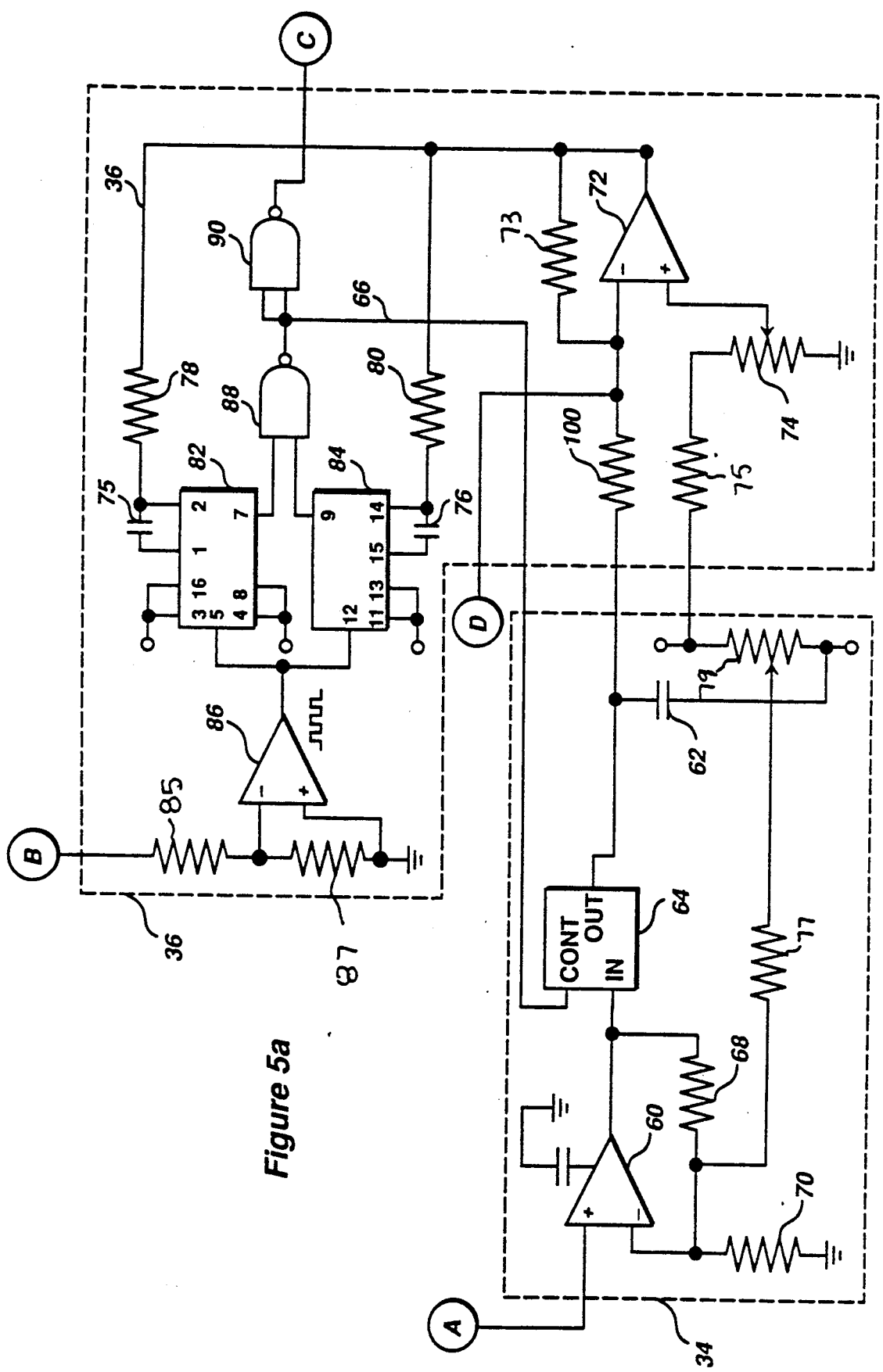
FIGS. 5a-5c are schematics of the components of the circuit of FIG. 3.
Figure 5B:
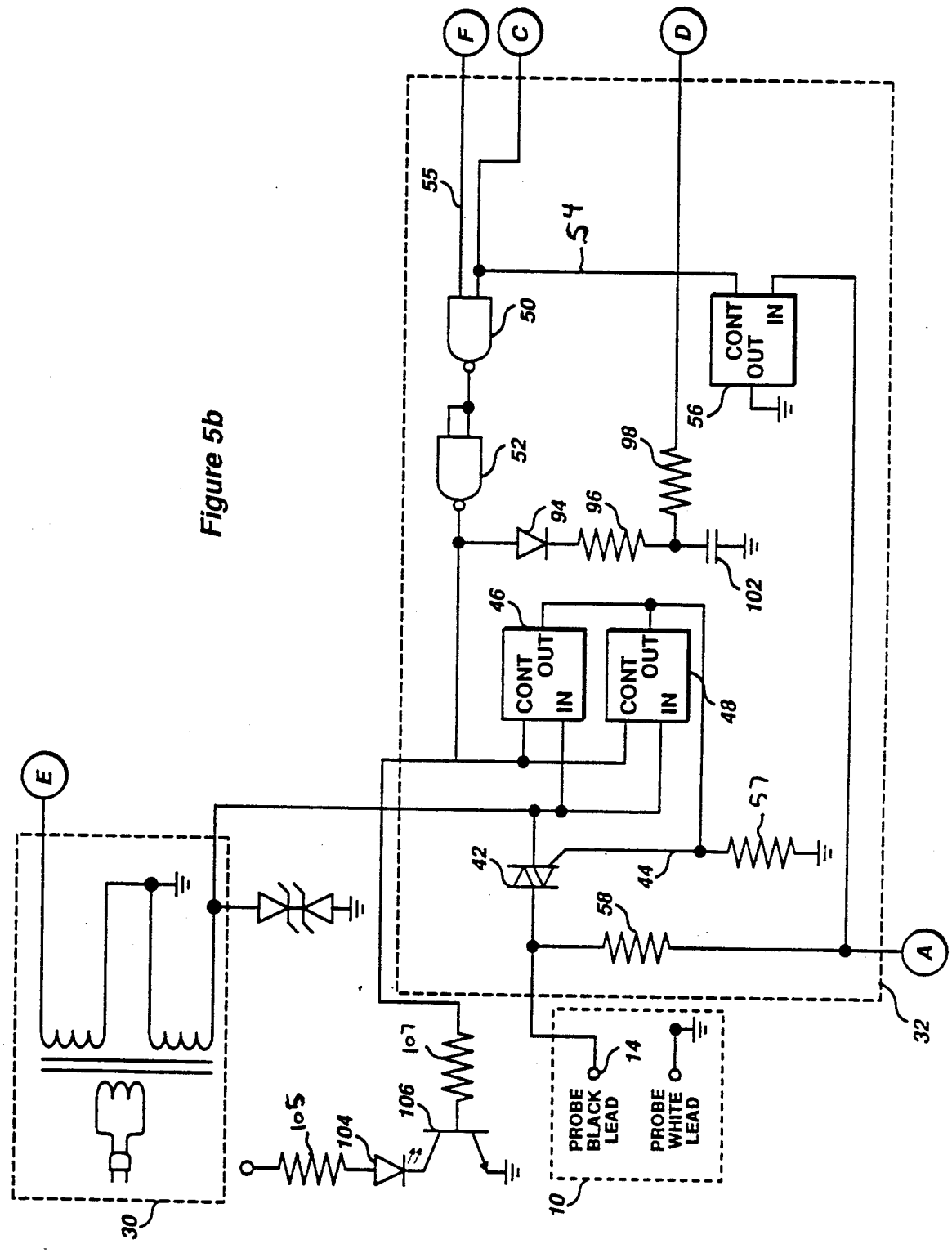
Figure 5C:
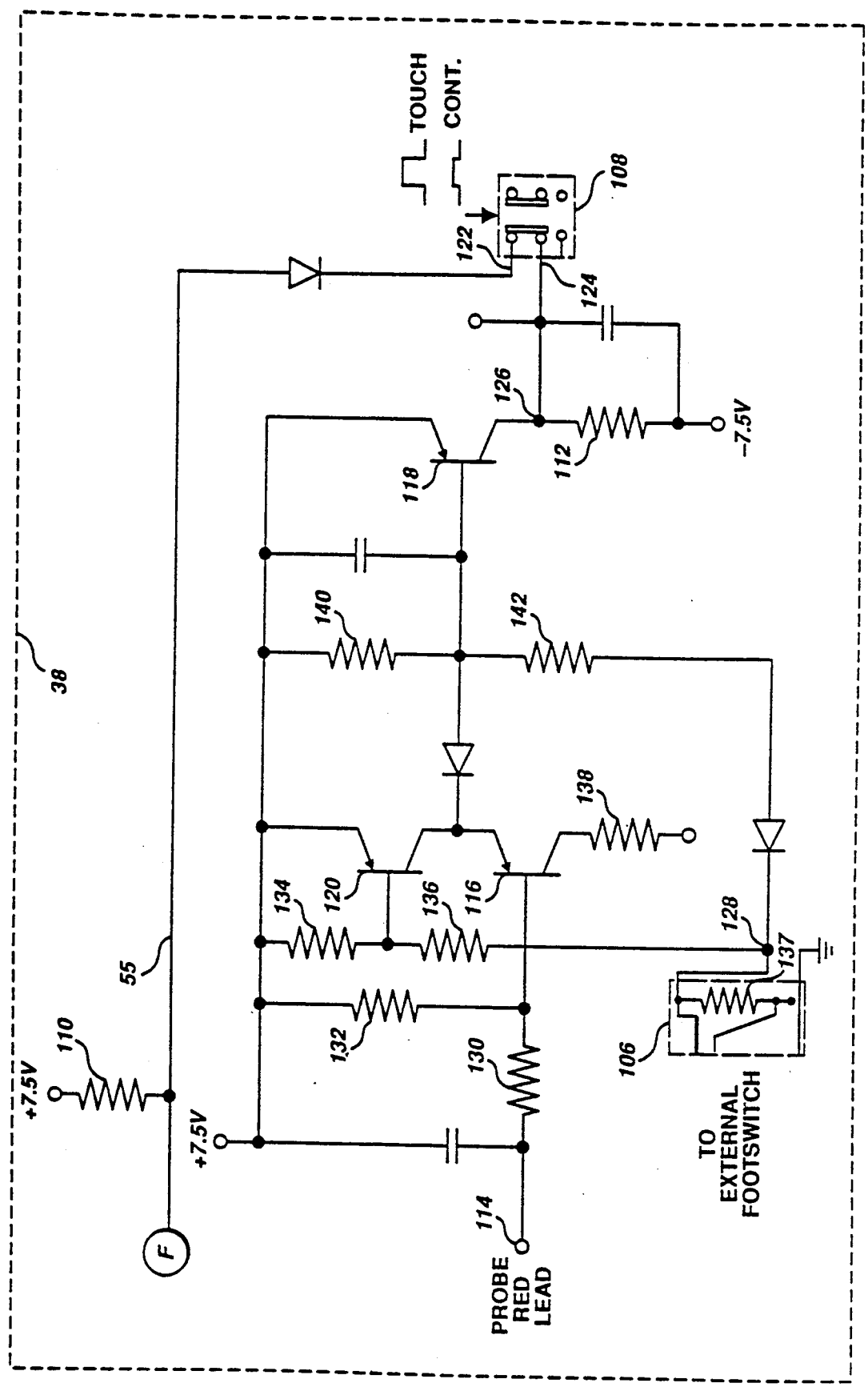

FIGS. 5a–5c are the detailed schematics of the circuit components shown in block diagram in FIG. 3. As shown in FIG. 5b, the AC power supply 30 is provided from the 2 volt winding of a transformer connected to AC line voltage. The AC line voltage may be 115 volts, 230 volts, or any other desired value. As shown in FIG. 7, the AC line voltage is input through a switch 40 to the transformer primary windings. The transformer secondary windings provide the AC power supply for heating the probe. The 8-volt winding is connected to DC to supply the electronic control circuit voltage shown in FIG. 6.

As shown in FIG. 5b, the switching circuit 32 includes a triac 42 having its input coupled to the 2-volt winding for providing AC power to the black lead of the tip 10, the black lead corresponding to the inner core member 14. The triac 42 is switched on and off through gate contact 44 coupled with the output of CMOS switches 46 and 48. The input voltage to switches 46 and 48 is the AC power supply voltage. The control pin being high for switches 46 and 48 closes them, causing the input voltage to be provided as the output; the control pin being low opens them. Switches 46 and 48 are controlled by inputs to NAND gate 50. One of the inputs to NAND gate 50 is from the manual control switch 38 shown in more detail in FIG. 5c, to manually deactivate the triac 42. The other input to NAND gate 50 is from the switch control and temperature selection circuit 36 shown in more detail in FIG. 5a. Having both inputs to NAND gate 50 high causes the output of NAND gate 52 to be high, turning switches 46 and 48 on and turning on triac 42. When either input is low, triac 42 is off.

LED 104 is held on whenever the triac 42 is conducting by bringing the base of transistor 106 high with the same input signal which controls gates 46 and 48. The output of LED 104 is visible to the user providing a visual indication of the amount of power being provided to probe tip 10. As the power being provided decreases, the light emitted by LED 104 decreases. Zener diodes are coupled to the power supply to control striking, as is known in the art.

The network of diode 94, resistors 96, 98, and 100, and capacitor 102 corrects for the temperature drift which takes place within the probe. The temperature drift is caused by indirect heating of a thermoelectric junction inside the probe, not within the tip 10, which is at a separate temperature. The resistive outer layer 12 of stainless steel material is coupled to ground in the probe, generally by being coupled to the probe white lead made of a separate material than the resistive outer layer 12. The coupling of the resistive outer layer 12 to the grounding white lead of a different material creates a second thermocouple junction at which a thermoelectric voltage is generated. Preferably, the grounding wire within the probe to which the resistive outer layer material is coupled is the same material as the inner core wire 14 within the probe, copper being the material used in one embodiment. The thermoelectric voltage generated at the grounding connection tends to counteract the voltage developed at the junction 22 in the tip. The voltage actually sensed will be the difference between these two thermoelectric voltages.

The network 96, 98, and 100 provides feedback to approximate a compensation for the temperature of the junction in the probe by varying the voltage on capacitor 62 to correspond to the power delivered to the tip. Capacitor 102 charges up at a rate determined by the RC time constant of 96, 98 and 100 and the time duration that the output of NAND gate 52 is high. If NAND gate 52 is on, power is being provided to the probe. The resistance and capacitor values are selected to compensate for a possible improper reading based on the power provided to the probe. Generally, the grounding connection within the probe is cold compared to the tip temperature. However, the amount of drift experienced will depend on the mechanical and electrical design of the probe.

The input pin of switch 56 is also coupled to the inner core member 14 of the probe 10. When the control line 54 is low, the switch 56 is off and does not affect the operation of the circuit, the thermoelectric voltage being provided as the input to amplifier 60, Node A of FIG. 5a. When the control pin 54 is high, switch 56 is turned on simultaneously with, or just prior to, NAND gate 50 causing the triac 42 to turn on. With the control line 54 high, the switch is closed, coupling the positive input to amplifier 60 to ground and limiting the voltage provided to amplifier 60 when triac 42 is conducting. Therefore, whenever triac 42 is on the output from resistor 58 is grounded, protecting the temperature-sensing circuit 34. Whenever the triac 42 is off, switch 56 is off and the thermoelectric voltage is sensed by the amplifier 60 temperature-sensing circuit 34.

As shown in FIG. 5a, temperature-sensing circuit 34 includes an operational amplifier 60 having its positive input coupled to the inner core member 14 of the tip 10 through Node A of FIG. 5b. The output of amplifier 60 is coupled to capacitor 62 for storing the sensed thermoelectric voltage of thermocouple junction 22. Although the sensing amplifier 60 is always connected to the tip 10 via resistor 58, the output is only coupled to capacitor 62 when the control pin 66 of switch 64 is high. When control pin 66 of switch 64 is low, the stored voltage on capacitor 62 is held constant, with little or no leakage. When the input pin 66 is high, switch 64 is closed and the output of amplifier 60 is coupled to the capacitor 62 through switch 64 to store the sensed thermocouple voltage as amplified by amplifier 60. The switch 64 is a two-way switch, permitting current to flow to or bleed off of capacitor 62. In one embodiment, the gain of amplifier 60 is approximately 1,000, resistor 68 having a value of 51 K ohms and resistor 70 having a value of 51 ohms, though other gain values and resistance values could be used, if desired.

As shown in FIG. 5a, amplifier 72 inverts and amplifies the difference between the voltage on capacitor 62 and the voltage on potentiometer 74. The value of potentiometer 74 is set by the user to select the desired operating temperature. Varying the resistance of potentiometer 74 thus causes a variation in the operating temperature to achieve any selected tip temperature.

As the voltage on capacitor 62 approaches the voltage on resistor 74, the output of 72 decreases, to decrease the power provided to the tip 10.

The switch control circuit 36 shown in detail in FIG. 5a controls the percentage of power provided to tip 10 as follows. Retriggerable one shots 82 and 84 receive inputs from amplifier 86. The output of amplifier 86 is approximately a square wave from the 8-volt winding of power supply 30. One of the retriggerable one shots 82 is triggered to become low by a negative to positive transition at its input pin and the other 84 is triggered to become low by a positive to negative transition at its input pin. Therefore, at each zero crossing of the power supply 30, one of the one shots 82 or 84 goes low.

When either of the one shots 82 or 84 goes low, the output from NAND gate 88 goes high causing the input pin 66 of switch 64 to go high to connect the sensing capacitor 62 to the amplifier 60, as previously described. Also, with the output of NAND gate 88 high, the output of NAND gate 90 is held low which holds input pin 54 at Node C of FIG. 5b to NAND gate 50 low, thus holding the triac 42 off. The thermocouple temperature is thus sensed with the triac 42 held off. The one shot output remains low for a selected time T after the zero crossing during which time the thermocouple voltage is stored on capacitor 62. Immediately after each zero crossing, whether from a positive to a negative or from a negative to a positive, the tip 10 is coupled to the temperature-sensing circuit 34 through action just described. Because each cycle has two zero crossings, one from positive to negative and the other from negative to positive, the temperature is sensed twice each cycle.

The duration of the time T that the tip is off and the temperature is sensed is controlled by the difference between the just sensed tip temperature and the selected temperature as follows. As previously discussed, the output of amplifier 72 is proportional to the difference between the voltage on capacitor 62 and the voltage on potentiometer 74 which corresponds to the selected operating temperature. The output of amplifier 72 is coupled to capacitors 75 and 76 via resistors 78 and 80, respectively. The timing lag, and thus duration of time T, of retriggerable one shots 82 and 84 coming high after the zero crossing is controlled by the RC time constraints of capacitor 75 and resistor 78 and capacitors 76 and resistor 80, respectively, as well as the voltage on line 36. The voltage on 36 is the only factor which changes. If line 36 has a high voltage, the capacitors will charge up faster, bringing the outputs of the one shots 82 and 84 high sooner in the cycle. The rate of charging is controlled by voltage on line 26, which is proportional to the difference between the selected temperature and the current temperature. When a selected charge is stored on capacitor 75, one shot 82 is brought back high after it is set low by the zero crossing at the input pin. Bringing one shot 82 high when the output of one shot 84 is also high causes the output of NAND gate 88 to go low, which simultaneously causes the switch 64 to be turned off to stop the temperature sensing and brings the input to NAND gate 50 high to turn on triac 42 to provide power to the probe. Triac 42 remains on, providing heating power to the probe for the remainder of that half-cycle, until the next zero crossing. At the next zero crossing, one shot 84 is brought low, causing the output of NAND gate 88 to go high. With the output of NAND gate 88 high, triac 42 is switched off and the temperature of the tip 10 is sensed and power not provided, as previously described.

As the tip 10 heats up, the difference between the selected temperature and the actual temperature decreases, resulting in a decrease in the difference between the voltage on capacitor 62 and the voltage of potentiometer 74. The output of amplifier 72 thus decreases, placing charge on capacitors 75 and 76 at a slower rate. The charge on the capacitors will reach the selected charge later in the cycle, thus increasing the duration of time T, the off time of triac 42 within a half-cycle. The amount of power provided within that half-cycle to heat the tip 10 through triac 42 is thus decreased. As the output of amplifier 72 decreases, the time duration from the zero crossing until the one shot 82 or 84 is brought high increases.

When the tip temperature equals approximately the selected temperature, the output of amplifier 72 will be relatively low, switching triac 42 on only for a small portion to the end of each half-cycle after the zero crossing and disconnecting the tip 10 from the power supply 30 for the majority of the half-cycle after the zero crossing. The temperature of the tip 10 will be held at the selected temperature, the amount of power being provided at each half-cycle being that required to maintain the selected temperature. If heat is taken from the tip, as may occur when the tip is applied to a work surface for soldering or for its intended medical purpose, the decrease in temperature will be immediately sensed as a lower thermoelectric voltage at junction 22.

The voltage on capacitor 62 will accordingly decrease. The difference between the voltage of potentiometer 74, which corresponds to the selected temperature, and the voltage of capacitor 62 will be amplified in that sensing portion of the cycle by amplifier 72. The capacitors 75 and 76 will charge a quicker and the one shot will go high sooner in the same half-cycle following the zero crossing, causing the triac 42 to provide greater power to the tip 10 in that half-cycle. The temperature is thus maintained at the selected temperature even if heat is taken from the tip 10.

The power provided in each half-cycle of the AC power supply is varied within the same half-cycle in which the temperature is sensed. Sensing and controlling the temperature within the same half-cycle causes accurate temperature control. Further, the temperature control is smooth because the tip 10 heats up based on the RMS power over the total on time of the cycle. The RMS heating power is controlled by changes in temperature because the triac is triggered later in the same cycle based on temperature sensed. During an off time each half-cycle, thermocouple temperature is sensed and held on capacitor 62.

One advantage of this circuit is that the temperature-sensing switch 64 is turned off, completing the sensing for that portion of the cycle in the first stage after the one shot 82 goes high. The amplifier input is not coupled to ground until later stages, after NAND gate 90 goes high and switch 56 is on and power is not provided to the tip 10 until triac 42 is on, many stages later, thus ensuring that the sensed voltage is isolated from transients occurring in the switching. The particular circuit arrangement provides built-in delays to ensure that the sensed voltage on capacitor 62 is contributed to only by, the thermocouple voltage and not by some switching or transient voltages.

Figure 6:
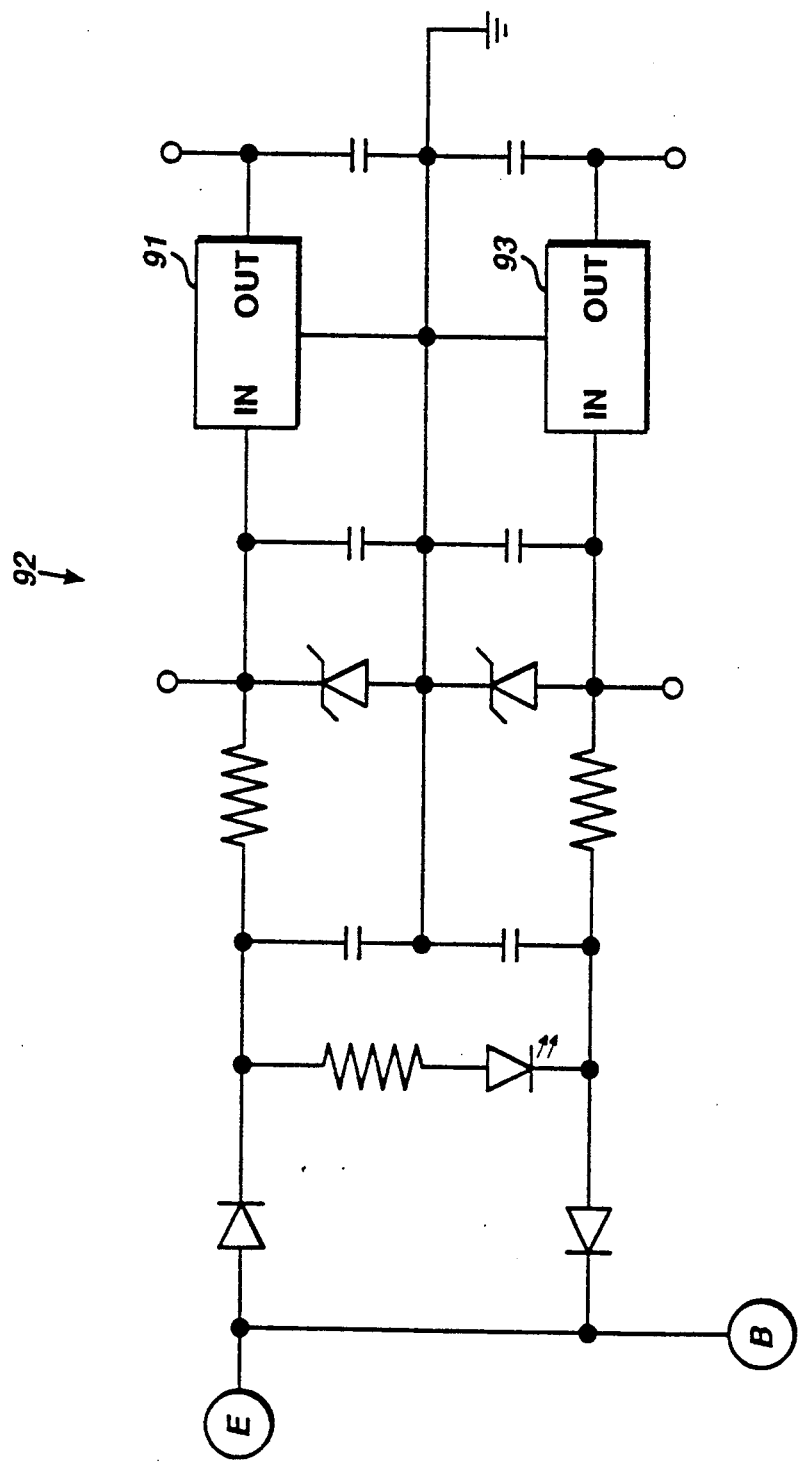
FIG. 6 is a schematic of the DC power supply for the circuits of the invention.
Figure 7:
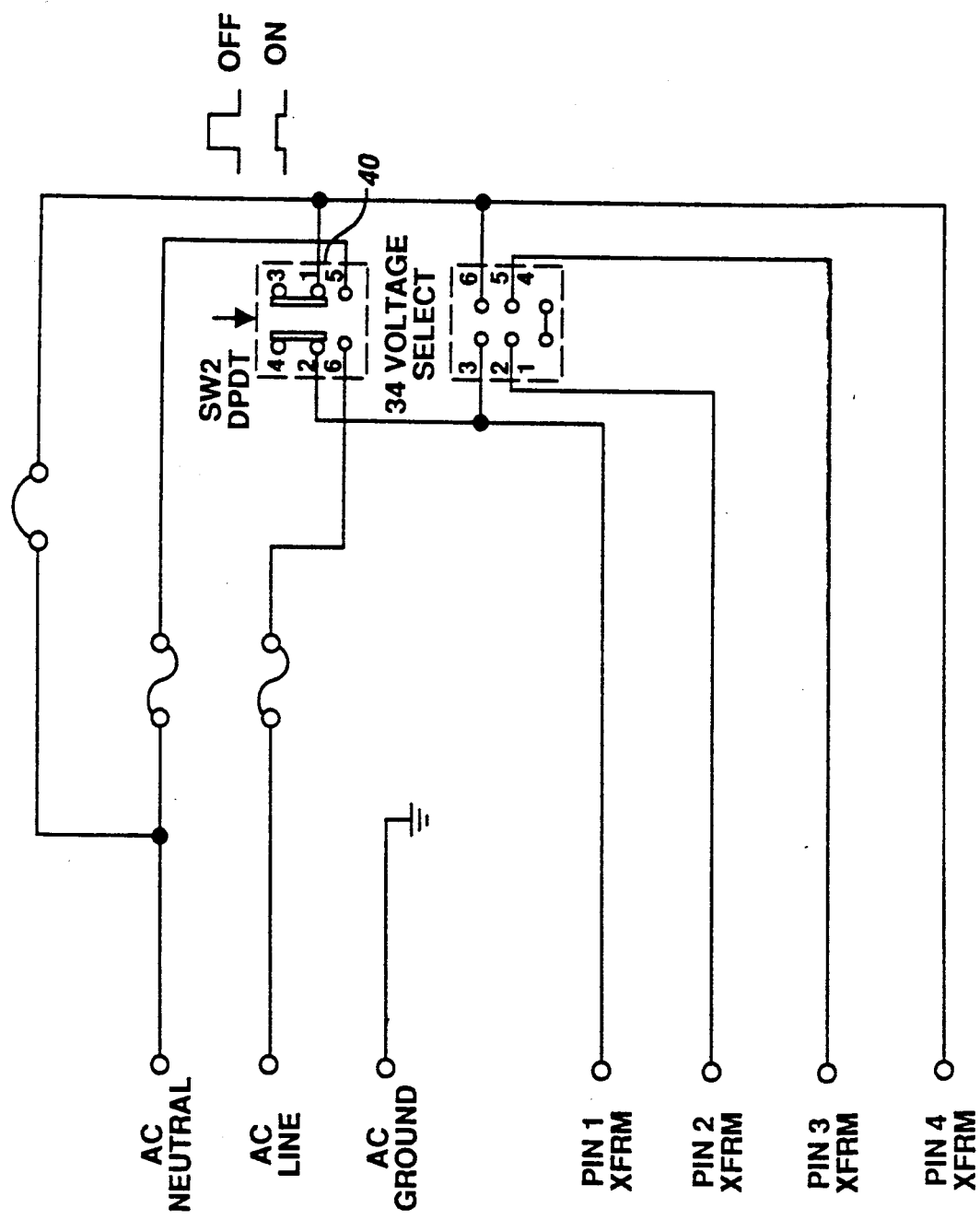
FIG. 7 is a schematic of the AC power source to the transformer for providing AC power to the circuits of the invention.

FIG. 6 is the regulated power supply for providing power to the circuit elements of FIGS. 5a-5c. The regulated power supply is of a standard design, the operation of which is readily apparent to those of ordinary skill in the art given the circuit schematic of FIG. 5. Circuit elements LM78L05ACZ and LM79205ACZ are the power supply circuits 91 and 93, available on the commercial market.

FIG. 5c is the detailed circuit for the manual on/off switch 38.

When switch 108 is depressed in the "cont." position the tip 10 is on and is heated under the control of the switch control circuit 36 as described herein. Depressing switch 108 creates an open circuit between pins 122 and 124, pulling line 55 up to approximately 7.5 volts through resistor 110, permitting triac 42 to turn on. With switch 108 in the raised "touch" position pins 122 and 124 are shorted together, bringing line 55 low, resistors 110 and 112 having the same value. The tip 10 is thus turned off.

Probe red lead 114 controls the tip 10, turning it on and off with the switch 108 in the "touch" position. The probe red lead 114 is coupled to a pressure activated switch in the handle of the probe. The lead 114 is coupled to ground when a user grips the probe by a pressure switch within the handle. Coupling the red lead 114 to ground turns on transistor 116, causing current to flow through its emitter from the base of transistor 118, thus turning on transistor 118. With transistor 118 on, 7.5 volts is placed on node 126, pulling line 55 high and permitting the tip to turn on and heat up under control of circuit 36. When the user releases his grip on the probe, lead 114 is open, transistors 116 and 118 are off and line 55 is held low, keeping the tip off. The tip is thus turned on and off by a user gripping or releasing the probe.

If a user desires to turn the tip on or off with a foot switch, an external foot switch 106 may be coupled to node 128. Coupling the foot switch 106 to node 128 disables the gripping switch coupled to the probe red lead 114. The probe red lead 114 is disabled because resistor 137 in the foot switch 106 always couples node 128 to ground, holding transistor 120 on. With transistor 120 on, transistor 118 cannot be turned on by transistor 116. The relative value of resistor 137 and resistors 136, 134, 140 and 142 are selected to ensure that transistor 120 is turned on but transistor 118 is held off. Thus state of transistor 118 is not affected by the probe red lead 114. The state of transistor 118 is controlled by the foot switch 106. When the foot switch is not activated, transistor 118 remains off. When the foot switch is activated, current is pulled through resistor 142, turning on transistor 118 and permitting the triac 42 to turn on under control of the switch control circuit 36 previously described. Even though a particular circuit for manual on/off switch 38 has been shown for disclosure purposes, any manual on/off switch of the many available in the art may be used.

In the circuit diagram shown on FIGS. 5a–5c, the following circuit components are suitable. The triac 42 is a TIC263D. Control switches 46, 48, 56, and 64 are a 4016 or a 4066. One shots 82 and 84 are each a 4528. Amplifiers 60, 72, and 86 are each a LM358. An LM-308A may also be used for amplifier 60, if desired. Capacitor 62 is 10 microfarads. Capacitor 102 is 1000 microfarads. Resistor 58 is 1K ohm. Resistors 78 and 80 are 68K ohms. Resistors 100, 85 and 87 are 20K ohms, Resistors 73 is 200K ohms, resistor 77 is 240K ohms and resistors 75, 137 and 134 are each 1M ohm. potentiometer 74 is a variable 100K ohms; and potentiometer 79 is a variable 1M ohms. Resistor 105 is 375 ohms; resistors 107, 130 and 136 are each 10K ohms; resistor 58 is 1K ohm; resistor 57 is 5.1K ohms; resistor 96 is 51K ohms; and resistor 98 is 510K ohms. Resistor 132 is 2M ohms and resistors 112, 140, 142 and 138 are 100K ohms. Suitable transistors are 2N3904 or 2N3906. Though specific components have been provided, any components which provide the same function will be suitable for use in the circuits of this invention.

Figure 8:
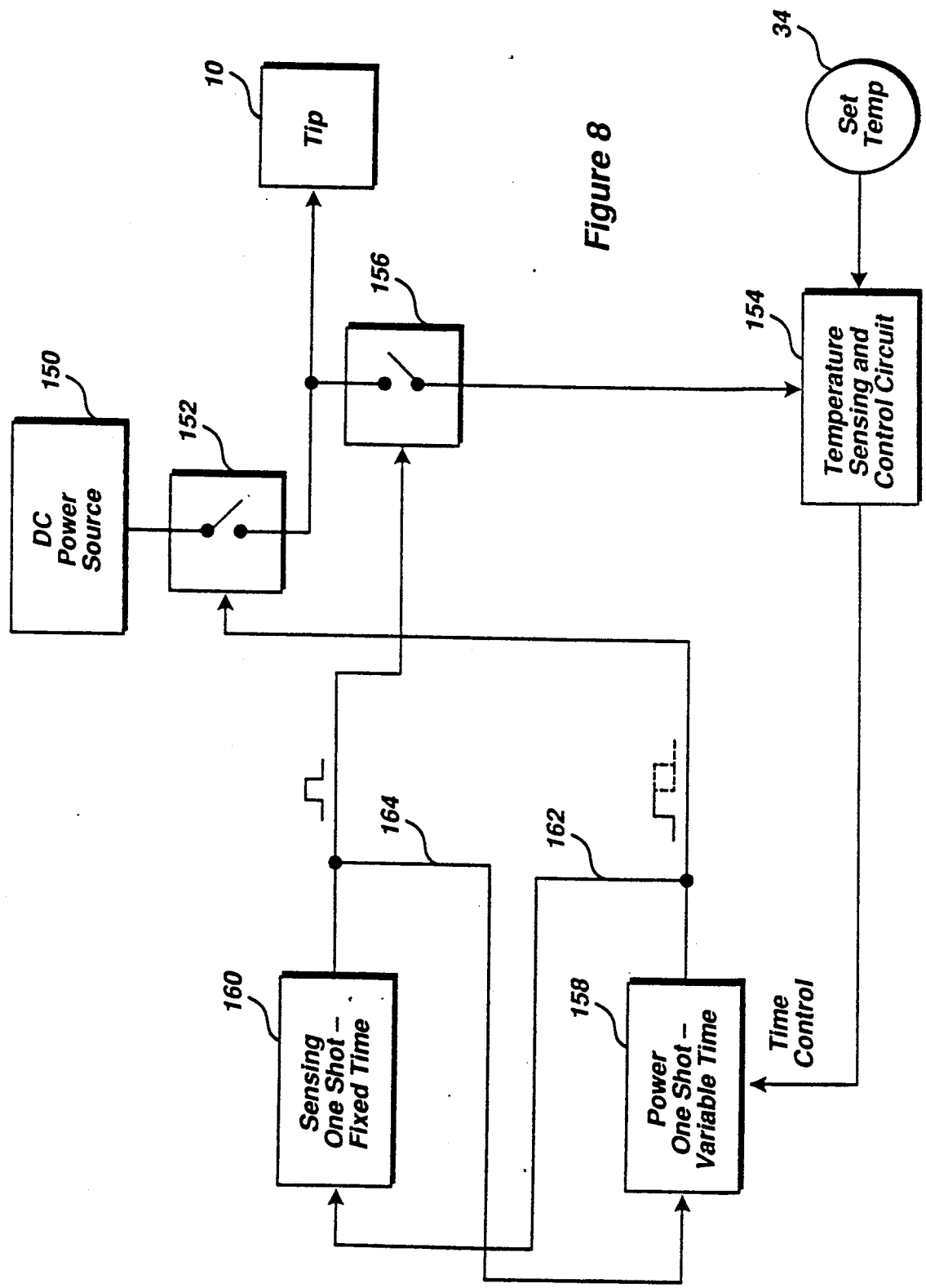
FIG. 8 is a block diagram of an alternative embodiment using a DC power source for heating the tip.

FIG. 8 illustrates an alternative embodiment having a DC power supply 150 for heating the tip 10. The DC power supply 150 is selectively coupled to heat the tip 10 through a transistor power switch 152. The tip 10 is coupled to a temperature and sensing control circuit 154 through a switch 156. The states of switches 152 and 156 are controlled by one shot circuits 158 and 160, respectively. The timing control of the one shot circuits 158 and 160 is controlled by temperature sensing and control circuit 154. One shot circuit 158 is on for a variable amount of time, depending upon the temperature of the tip. If the temperature is low, the one shot 158 remains on for a longer period of time to provide additional power to tip 10 for heating. A timing circuit within temperature sensing and control circuit 154 selectively turns on sensing one shot 160 for a fixed period of time on a selected cycle. The power time circuit 158 is turned off to permit temperature sensing at the selected intervals. After the temperature is sensed at the sampling interval, the power one shot circuit 158 activates switch 152 to reconnect the DC power source 150 for a time period having a duration based on the difference between the tip temperature and the preselected temperature set by the user. The temperature sensing and control circuit 154 thus controls the percentage of time during which power supplied to heat the tip based on the difference between the preselected temperature and the tip temperature.

The time interval for which switch 152 remains activated is limited to a maximum value to permit sensing of the temperature at selected reoccurring sampling intervals. As the temperature increases, towards the preselected temperature, the variable time one shot 158 activates the power switch 152 for shorter intervals of time. More frequent or longer temperature sensing intervals may occur if desired, though this is not necessary. The temperature is therefore more precisely controlled as the tip temperature approaches the preselected temperature.

In one embodiment, one shots 158 and 160 are each triggered on a positive to negative transition of the trigger input, ensuring that when one of the one shots comes on, the other is automatically turned off by feedback through output lines 162 and 164, respectively, as shown in FIG. 8. The principles of operation for the detailed circuit diagrams of FIGS. 4 and 5a–5c may be used to construct the specific circuit of FIG. 8. For some circuit components, an identical circuit element may be used. For example, the temperature sensing circuit 34 and switch control and temperature selection circuit 36 may be used to provide the temperature sensing and control circuit 154 of FIG. 8. Similarly, the use of an RC network coupled to an amplifier may be used to control the variable time duration for the on time of the power one shot 158. A multivibrator, oscillator or other switching device may be included to ensure that the sensing one shot 160 is turned on to activate switch 156 at preselected time intervals using circuit elements and principles well known to those of ordinary skill in the art given the circuit description and disclosure herein.

The advantage provided by the structure of this invention is the simultaneous heating and temperature-sensing capability within a single cycle of the power supply. In particular, the use of two different materials, an insulated core of high-conductivity surrounded by a mechanically tough material of low-conductivity for heating, gives rise to a thermoelectric voltage potential which may be amplified and used to control the temperature. While the particular circuits shown and described herein have been found suitable for providing the desired temperature control, other circuits which perform the same function may also be used.

I claim:

1. An apparatus for controlling the tip temperature of a heated probe, comprising:
    a tip having an electrically conductive inner core member of a first material and a resistive heating member of a second material, said core member and said resistive heating member being connected to each other at a distal end of said tip to form a thermocouple at said tip;
    a power source means selectively coupled to said tip for passing current through said tip;
    a sensing circuit means selectively coupled to said thermocouple of said tip for sensing a voltage potential between said core member and said resistive heating member that is small with respect to the voltage that said power source applies to said tip to provide a temperature measurement of said tip based on said thermocouple voltage potential; and a switching means for selective coupling said tip to said power source for heating said tip or to said sensing circuit for sensing the temperature of said tip to maintain said tip at a preselected temperature so that said thermocouple voltage is used by said sensing circuit to provide an indication of the temperature of said tip only when said power source if not passing current through said tip.

2. The apparatus according to claim 1 wherein said switching means includes a user controllable potentiometer for setting said preselected temperature, the voltage across said potentiometer being proportional to said preselected temperature, and a voltage comparing means for comparing a voltage across said potentiometer to said thermocouple voltage, an output from said voltage comparing mean being used to determine the heating power applied to said probe.

3. The apparatus according to claim 1 wherein said power source provides alternating current to heat said tip and said switch means controls the percentage of time of each cycle during which power is applied to said tip based on the difference between said preselected temperature and said tip temperature.

4. The apparatus according to claim 3, further including a control circuit means for controlling said switch means to couple said thermocouple to said sensing circuit and disconnected said power supply from said tip at each zero crossing of said power supply voltage and to couple said tip to said power supply at a first time after said zero crossing, the difference in time between said zero crossing and said first time being based on the difference between said tip temperature and said preselected temperature, said tip being coupled to said power supply from said first time until the next zero crossing of said power supply.

5. The apparatus according to claim 4 wherein said control circuit includes a one-shot coupled to said power supply which goes low at zero crossing and remains low for a selected time based on the difference between said preselected temperature and said tip temperature, said selected time increasing as said tip temperature approaches said preselected temperature.

6. The apparatus according to claim 3 wherein the power supply coupled to said tip is an alternating current power supply and the temperature is sensed at least once each cycle.

7. The apparatus according to claim 6 wherein the percentage of power from a single cycle applied to heat said tip is determined based on the temperature sensed with the same cycle.

8. The apparatus according to claim 1, further including a temperature compensation circuit coupled to said sensing circuit for compensating for the temperature of the thermocouple formed at the ground junction between said resistive outer layer and a ground wire within said probe.

9. The apparatus according to claim 1 wherein said resistive heating member is an outer layer which contacts the surface to be heated.

10. The apparatus according to claim 1 wherein said resistive heating member is spaced from the outer layer which contacts said tip by an electrically-insulating member.

11. The apparatus according to claim 1 wherein said resistive heating element is a coil surrounded by an outer layer, heat having conducted from said coil to a surface region of said tip.

12. The apparatus according to claim 1 wherein said power source provides electrical current to heat said tip and said switch means controls the percentage of time during which power is applied to said tip based on the difference between said preselected temperature and said tip temperature.

13. The apparatus according to claim 1, further including a control circuit means for controlling said switch means to couple said thermocouple to said sensing circuit and disconnect said power supply from said tip at recurring sampling intervals during which the temperature is sensed by the said sensing circuit and to reconnect said power supply to the tip for time periods having a duration based on the difference between said tip temperature and said preselected temperature.

14. The apparatus according to claim 1 wherein said power source provides direct current to heat said tip and said switch means selectively couples said tip to said sensing circuit for sensing the temperature and couples said tip to said power source for a variable time based on the temperature of said tip just previously sensed.

15. A method of controlling the temperatue of a heated tip, said tip including a n electrically conductive inner core member of a first material and a resistive heating member of a seocn dmaterial, surrounding said inner core, sid core member and sid resisitive heating member being connetd to each other at a distal end of sid tip to form a thermocouple at said tip, comprising:

passing a heated current through sid tip for heating sid tip to a preselected temperature;

sensing the voltage at a thermocouple junction within said tip when said heating current is not passing through said tip, sid voltage corresponding to the temperature at said thermocouple junction and being small with respect to the voltage from said tip when said heating current is being passed through said tip;

comparing said sensed voltge with a voltage corresponding to a preselected temperature set from said tip to attain when heating current is not passing through said thermocouple junction; and varying the time duration of the heating current passing through said tip based on said comparing steps so that the voltage at said thermocopule is sensed to provide an indication of the temperature of said tip only when said heating current is not passing through said tip.

16. The method according to claim 15, further including said heating current is alternating current and said sensing step is performed at lest once each cycle and the step of varying the time duration of the heating current occurs within the same cycle as said sensing sep.

17. The method according to claim 15 wherein said heating current is direct current and said sensing step occurs on a predetermined timed cycle.

18. An apparatus for heating a probe and controlling the temperature to which said probe is heated, comprising:

a heating element, said heating element including an electrically conductive first member joined in series to an electrically conductive second member, said first and second members being dissimilar materials such that a voltage is generated at a junction between said first and second members, said junction being a thermocouple junction such that the voltage level generated is proportional to the temperature at said junction, said heating element being sufficiently resistive that current passing through said first and second members generates heat;

a power source providing electric powers to said heating element;

a voltage sensing circuit coupled to said heating element to sense a voltage generated at said thermocouple junction that is small with respect to the voltage that said power source provides to said heating element; and a switching circuit which connects said voltage sensing circuit to said thermocouple junction when power is not being applied to said heating element, and which automatically disconnects said power source from said heating element when said voltage sensing circuit is coupled to the heating element so that said voltage generated at said thermocouple junction is used by said voltage sensing circuit to provide an indication of the temperature of said tip only when said power source is not providing electric power to said heating element.

19. The apparatus according to claim 18 wherein said switching circuit causes said power source to be automatically disconnected from said heating element when said voltage sensing circuit is coupled to the heating element.

20. The apparatus according to claim 18 wherein said first and second dissimilar materials include copper and steel, respectively, and said heating element is a tip portion of a dental probe, said heat being generated by resistive heating of said steel material.

* * * * *